United States Patent
Takase et al.

(10) Patent No.: US 7,850,603 B2
(45) Date of Patent: Dec. 14, 2010

(54) ENDOSCOPE FOR STERILIZING BUILT-IN ELONGATED CHANNEL WITH HIGH-TEMPERATURE AND HIGH-PRESSURE VAPOR

(75) Inventors: Seisuke Takase, Tokyo (JP); Hiroki Moriyama, Tokyo (JP); Takehiro Nishiie, Tokyo (JP); Masaaki Miyagi, Tokyo (JP)

(73) Assignee: Olympus Corporation, Tokyo (JP)

( * ) Notice: Subject to any disclaimer, the term of this patent is extended or adjusted under 35 U.S.C. 154(b) by 631 days.

(21) Appl. No.: 11/842,771

(22) Filed: Aug. 21, 2007

(65) Prior Publication Data
US 2007/0293723 A1   Dec. 20, 2007

Related U.S. Application Data

(63) Continuation of application No. 10/896,804, filed on Jul. 22, 2004, now abandoned.

(30) Foreign Application Priority Data

Jul. 24, 2003   (JP) ............................. 2003-201235

(51) Int. Cl.
*A61B 1/04*   (2006.01)
(52) U.S. Cl. .................. 600/133; 600/101; 600/153; 600/156; 600/158; 600/159
(58) Field of Classification Search ................ 600/101, 600/133, 158–159; 422/26, 267
See application file for complete search history.

(56) References Cited

U.S. PATENT DOCUMENTS

| | | | |
|---|---|---|---|
| 4,545,369 A | 10/1985 | Sato | |
| 4,771,766 A | 9/1988 | Aoshiro et al. | |
| 5,749,829 A | 5/1998 | Yokoi et al. | |
| 5,871,441 A | 2/1999 | Ishiguro et al. | |
| 5,891,014 A | 4/1999 | Akiba | |
| 6,412,334 B1 | 7/2002 | Kral et al. | |
| 2002/0013510 A1 | 1/2002 | Moriyama | |
| 2002/0072653 A1 | 6/2002 | Ishizuka | |
| 2002/0128535 A1 | 9/2002 | Kikuchi et al. | |
| 2002/0128539 A1 | 9/2002 | Higuma et al. | |
| 2003/0149339 A1 | 8/2003 | Ishibiki | |
| 2006/0276691 A1 | 12/2006 | Forkey et al. | |

FOREIGN PATENT DOCUMENTS

| | | |
|---|---|---|
| JP | 10-234658 | 9/1998 |
| JP | 11-32988 | 2/1999 |
| JP | 2000-51323 | 2/2000 |
| JP | 2001-258832 | 9/2001 |
| JP | 2003-174997 | 6/2003 |
| WO | WO 00/18521 | 4/2000 |

*Primary Examiner*—Matthew J Kasztejna
(74) *Attorney, Agent, or Firm*—Scully, Scott, Murphy & Presser, P.C.

(57) ABSTRACT

An endoscope according to the present invention includes an endoscope main body, in which a channel having at least one end communicated with the outside is inserted and which is covered with an exterior member, and a communicating hole which is arranged in the halfway of the channel and which introduces vapor in the channel so as to sterilize the channel with the vapor.

9 Claims, 6 Drawing Sheets

ENDOSCOPE FOR STERILIZING BUILT-IN ELONGATED CHANNEL WITH HIGH-TEMPERATURE AND HIGH-PRESSURE VAPOR

This application is a continuation application of U.S. application Ser. No. 10/896,804 filed on Jul. 22, 2004 which claims benefit of Japanese Application No. 2003-201235 filed on Jul. 24, 2003, the entire contents of each of which are incorporated herein by this reference.

BACKGROUND OF THE INVENTION

1. Field of the Invention

The present invention relates to an endoscope for endoscope examination and diagnosis.

2. Description of the Related Art

Recently, endoscopes are being widely used for examination and diagnosis of the body cavity and plant inspection in both the medical field and the industrial field. In particular, in the medical field, sterilization is necessary to prevent infectious disease after examination with the endoscope.

Further, recently, a method using the sterilization with high-temperature and high-pressure vapor is widespread. The sterilization with high-temperature and high-pressure vapor is advantageous in running costs and environmental measures.

For example, Japanese Unexamined Patent Application Publication No. 2000-51323 discloses a sterilization method for preventing damage to an outer casing of an endoscope due to a pressure difference between the inside and the outside of the endoscope when the endoscope is sterilized with the high-temperature and high-pressure vapor.

Further, Japanese Unexamined Patent Application Publication No. 2001-258832 discloses an endoscope comprising an elongated channel having an end which is opened to the outside of the endoscope.

SUMMARY OF THE INVENTION

According to the present invention, an endoscope comprises:

an endoscope main body, having therein a channel having at least one end communicated with the outside, the endoscope being covered with an exterior member; and a communicating hole which is arranged in the halfway of the channel and which introduces vapor in the channel so as to sterilize the channel with the vapor.

Other features and advantages of the present invention will be obvious by the following.

BRIEF DESCRIPTION OF THE DRAWINGS

FIGS. 1 to 5 relate to a first embodiment of the present invention,

FIGS. 7A and 7B relate to a third embodiment of the present invention.

DESCRIPTION OF THE PREFERRED EMBODIMENTS

First Embodiment

Figure 1:
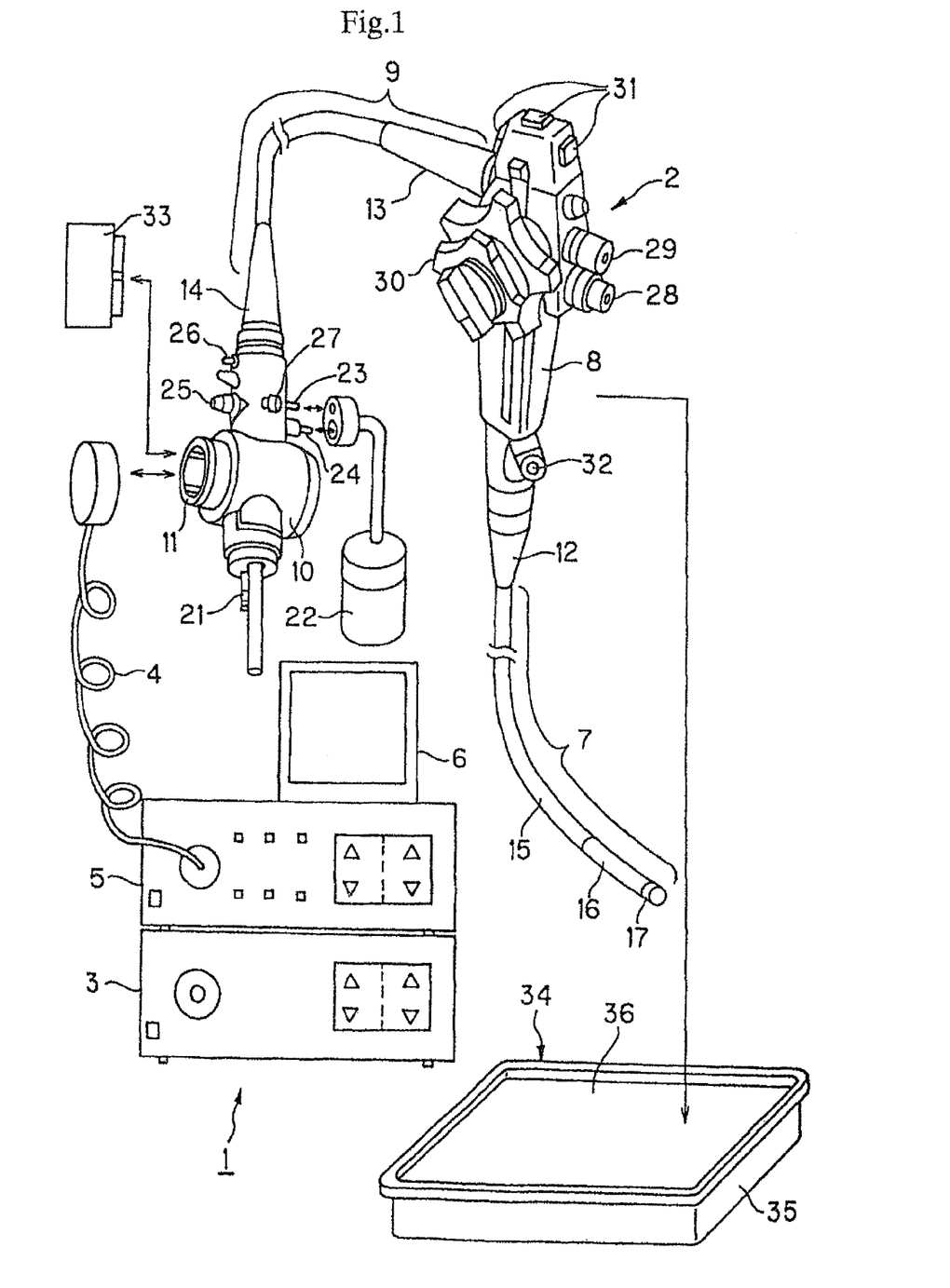
FIG. 1 is a diagram showing the entire structure of an endoscope apparatus having an endoscope according to the first embodiment of the present invention.

Referring to FIG. 1, an endoscope apparatus 1 comprises: an endoscope 2 having, e.g., image pick-up means; a light source device 3 which is detachably connected to the endoscope 2 and which supplies illuminating light to a light guide arranged to the endoscope 2; a video processor 5 which is connected to the endoscope 2 via a signal cable 4, controls the image pick-up means of the endoscope 2, and processes a signal obtained by the image pick-up means; and a monitor 6 which displays a video image corresponding to a subject image outputted from the processor 5. After the endoscope 2 is used for observation or treatment, the endoscope 2 further comprises a component, e.g., an outer casing, which is resistant to vapor with high temperature and high pressure so as to enable the sterilization with high-temperature and high-pressure vapor after cleaning.

The endoscope 2 is flexible, and comprises: an elongated inserting portion 7 which can be inserted in an examinee (specifically, body cavity); an operating portion 8 which is connected to the base end side of the inserting portion 7; a connecting cord (universal cord) 9 which is flexible and is extended form the side portion of the operating portion 8; a connector portion 10 which is arranged to an end of the connecting cord 9 and is detachably connected to the light source device 3; and an electric connector portion 11 which is arranged to the side portion of the connector portion 10 and to which the signal cable 4 connected to the processor 5 is detachably connected.

The electric connector portion 11 has an air port 37 (refer to FIG. 4A) which communicates with the inside and the outside of the endoscope 2.

A connecting portion between the inserting portion 7 and the operating portion 8 has a protection boot 12 on the inserting portion side, having an elastic member for preventing the sharp bending operation of the connecting portion. A connecting portion between the operating portion 8 and the connecting cord 9 has a protection boot 13 on the operating portion side. A connecting portion between the connecting cord 9 and the connector portion 10 has a protection boot 14 on the connector portion side.

The inserting portion 7 comprises: a flexible tube portion 15 which is flexible and soft; a bending portion 16 which is arranged to the distal side of the flexible tube portion 15 and is bent by the operation of the operating portion 8; and a hard tip portion 17 which is arranged to the distal side of the bending portion 16 and has an observing optical system and an illuminating optical system (which are not shown).

The tip portion 17 comprises an air/water feed nozzle 18 (shown in FIG. 4A) which spouts out a cleaning fluid or air to an optical member on the outer surface of the observing optical system (not shown) by feeding the air/water; and a suction portion, as an opening on the distal side of a treatment tool channel (not shown), into which a treatment tool arranged to the inserting portion 7 is inserted, for sucking fluid in the body cavity. Further, the tip portion 17 comprises a liquid feed opening which is opened to an observing target and which spouts out the liquid.

The connector portion 10 has an air feed cap 21 which is detachably connected to an air feed source (not shown) incorporated in the light source device 3. And the connector portion 10 has a water feed tank pressurizing cap 23 and a liquid feed cap 24 which are detachably connected to a water feed tank 22 as a liquid feed source.

Further, the connector portion 10 comprises a suction cap 25 which is connected to a suction source (not shown) for suction from the suction port. Furthermore, the connector portion 10 comprises: an injecting cap 26 which is connected to water feed means (not shown) which feeds water from the liquid feed opening.

In addition, the connector portion 10 comprises: an earth terminal cap 27 for feeding back the leakage current to a high-frequency treating device in the case where the high-frequency current is leaked in the endoscope when the high frequency treatment is performed.

The operating portion 8 comprises: an air/water feed operating button 28 which controls the water feed operation; a suction operating button 29 which controls the suction operation; a bending operating knob 30 for the bending operation of the bending portion 16; a plurality of remote switches 31 which remotely control the video processor 5; and a treatment tool inserting port 32 as an opening communicated with the treatment tool channel.

A waterproof cap 33 with a pressure adjusting valve is detachably connected to the electric connector portion 11 of the endoscope 2. The waterproof cap 33 with the pressure adjusting valve has a pressure adjusting valve (not shown).

In sterilization with high-temperature and high-pressure vapor, the endoscope 2 is placed in a storage case 34 for sterilization.

The storage case 34 comprises: a tray 35 which is opened on the top surface side and which places therein the endoscope 2; and a cover member 36 which covers the top surface side of the tray 35.

A plurality of air holes (not shown) are arranged to the tray 35 and the cover member 36. The steam passes through the air holes.

Figures 2A, 2B:
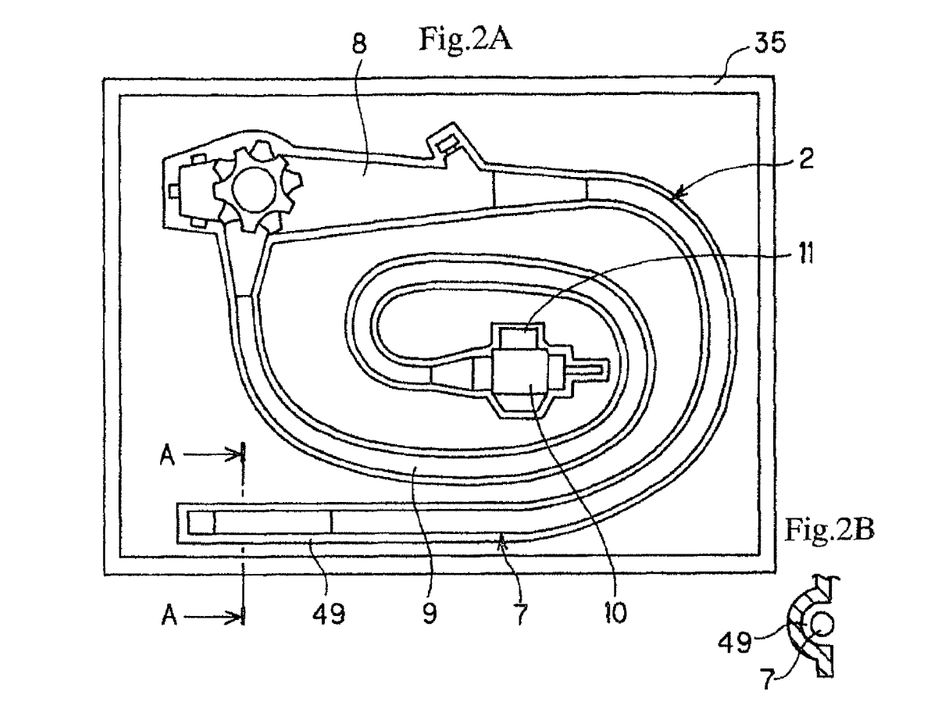
FIG. 2A is a diagram showing a state in which the endoscope is placed in a tray shown in FIG. 1.
FIG. 2B is a cross-sectional view showing an A-A cross section at the position of an inserting portion shown in FIG. 2A.

Referring to FIG. 2A, the tray 35 has a concaved portion (groove portion) corresponding to the shape of the endoscope 2 and, along the concaved portion, a position regulating portion (abbreviated to a regulating portion) 49 is formed to the tray 35 so as to position the components of the endoscope 2. The regulating portion 49 is formed so that the components in the endoscope 2 are positioned at predetermined positions. For example, an A-A cross section at the position of the inserting portion 7 in FIG. 2A is shown in FIG. 2B. The regulating portion 49 is formed with a concaved portion which is substantially U-shaped with a diameter slightly larger than the outer diameter of the inserting portion 7 so as to place the inserting portion 7.

Figure 3:
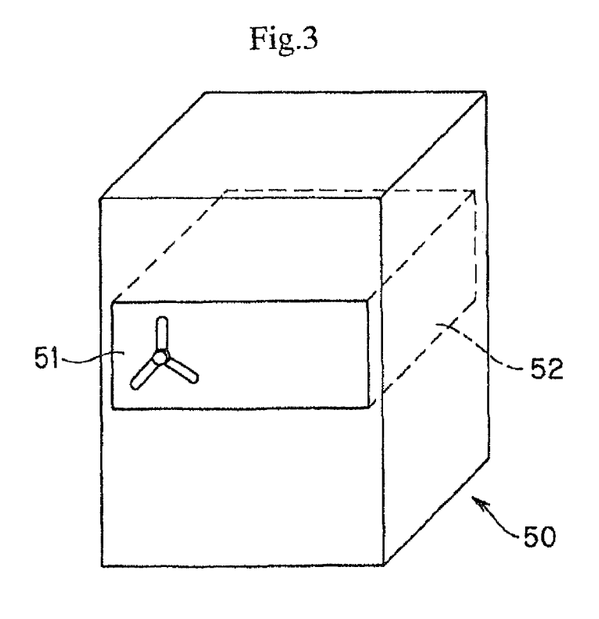
FIG. 3 is a diagram showing the structure of a sterilizing device with high-temperature and high-pressure vapor, which sterilizes the endoscope shown in FIG. 1 with the high-temperature and high-pressure vapor.

FIG. 3 shows a sterilizing device 50 with high-temperature and high-pressure vapor which places the endoscope 2 and sterilizes it with high-temperature and high-pressure vapor according to the first embodiment.

The sterilizing device 50 with high-temperature and high-pressure vapor is box-shaped, and has a door 51 arranged to the front side thereof. The door 51 is opened and, then, a chamber 52 for sterilization with high-temperature and high-pressure vapor is arranged. The storage case 34 is installed in the chamber 52 for sterilization with high-temperature and high-pressure vapor, thereby sterilizing the endoscope 2. The storage case 34 includes the tray 35 which places therein the endoscope 2 and the cover member 36 which covers the tray 35.

The chamber 52 may be shaped so that it just includes one storage case 34 having the endoscope 2.

A typical condition is as follows for sterilization with high-temperature and high-pressure vapor using the sterilizing device 50 with high-temperature and high-pressure vapor or the like.

According to the American national standard ANSI/AAMI ST37-1992 approved by American National Standards Institute and issued by The Association for the Advancement of Medical Instrumentation, the sterilizing condition with high-temperature and high-pressure vapor is 4 min at a temperature of 132° C. in the pre-vacuum type and is 10 min at a temperature of 132° C. in the gravity type.

The temperature condition in the sterilizing step of sterilization with high-temperature and high-pressure vapor varies depending on the sterilizing time and the type of the sterilizing device with high-temperature and high-pressure vapor. Generally, the temperature condition in the sterilizing step of sterilization with high-temperature and high-pressure vapor is set within the range of 115° C. to 138° C. The temperature of one sterilizing device can be set to 142° C.

The time condition varies depending on the temperature condition in the sterilizing step. Generally, the time condition is set to 3 to 60 min. The time condition can be set to 100 min depending on the type of the sterilizing device.

In the sterilizing step, the pressure in the sterilizing room is generally set to +0.2 MPa for the atmospheric pressure.

Normally, the sterilizing step with high-temperature and high-pressure vapor in the pre-vacuum type comprises: a pre-vacuum step of decreasing the pressure in the sterilizing room which places therein the sterilized device before the sterilizing step; and a sterilizing step of then sterilizing the sterilizing room by feeding vapor with high-temperature and high-pressure. The pre-vacuum step is the step for permeating the vapor throughout the sterilized device in the subsequent sterilizing step, and thus the vapor with high-temperature and high-pressure spreads to the entire sterilized device by decreasing the pressure of the sterilizing room.

The pressure in the sterilizing room in the pre-vacuum is generally −0.07 MPa to −0.09 MPa for atmospheric pressure.

In order to dry the sterilized device after sterilization, some pre-vacuum type comprises a step of drying the sterilizing room which is set to decrease the pressure again after the sterilizing step. In the drying step, the pressure in the sterilizing room is decreased, the vapor is excluded from the sterilizing room, and thus the drying process of the sterilized device in the sterilizing room is promoted. In the drying step, the pressure in the sterilizing room is generally set to a range from −0.07 MPa to −0.09 MPa for atmospheric pressure.

Figures 4A, 4B:
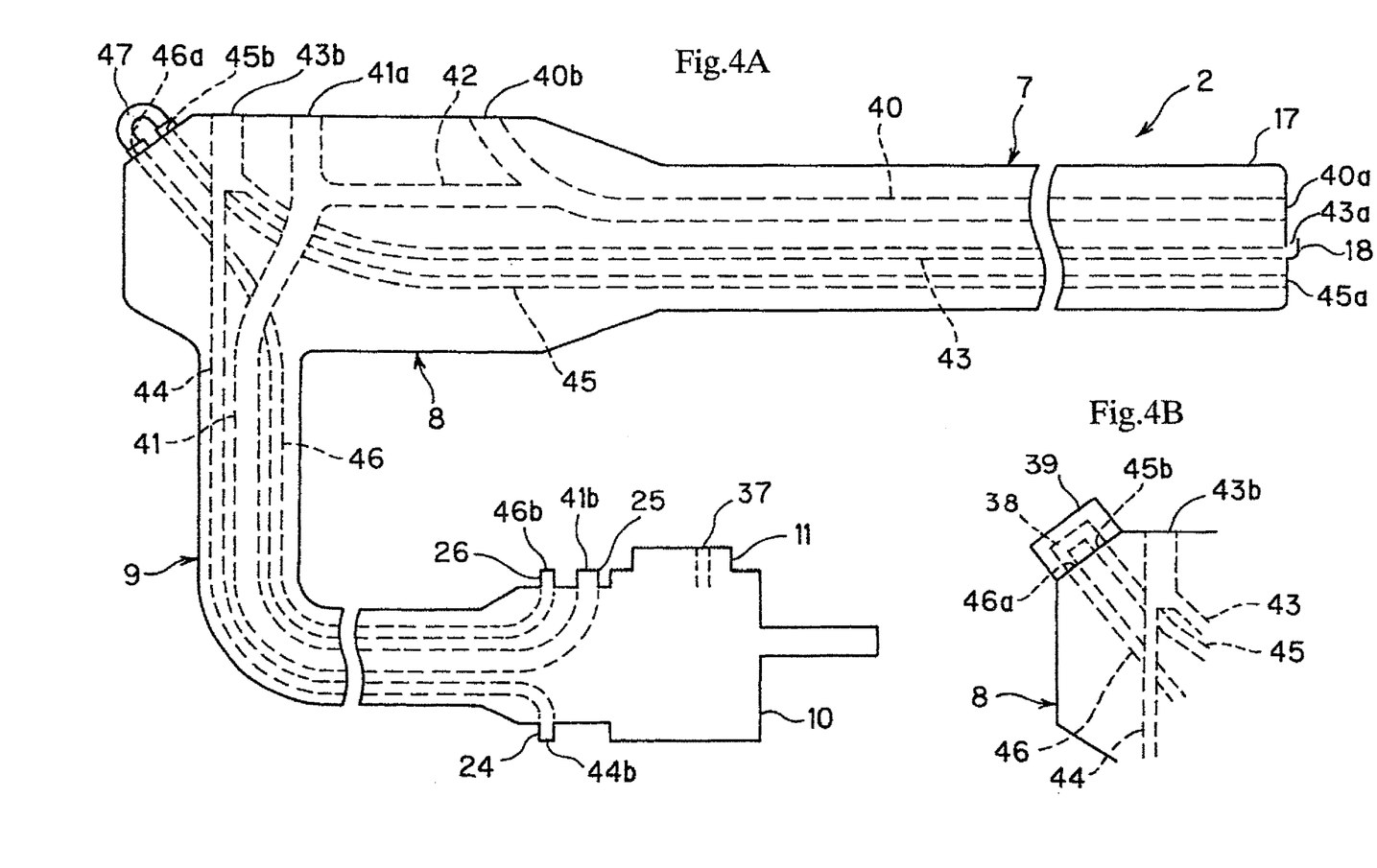
FIG. 4A is a diagram showing the structure of a channel system arranged to the endoscope shown in FIG. 1 and a part thereof according to a first modification.
FIG. 4B is a diagram showing the structure of a channel system arranged to the endoscope shown in FIG. 1 and a part thereof according to a second modification.

Next, a description is given of the structure having the feature of the endoscope 2 according to the first embodiment of the present invention with reference to FIG. 4A.

FIG. 4A schematically shows various channel systems including the endoscope 2.

A channel 40 is mainly provided in the inserting portion 7. A front end 40a thereof is opened to the outside at the tip portion 17. A back end 40b thereof is opened to the outside at the operating portion 8. The channel 40 is for inserting the treatment tool or for suction.

A channel 41 is mainly provided in the connecting cord 9. A front end portion 41a thereof is opened to the outside at the operating portion 8. A back end 41b thereof is opened to the outside at the connector portion 10 by the suction cap 25. The channel 41 is for suction, for example.

A channel 42 is mainly provided in the operating portion 8. A front end of the channel 42 is communicated with the back end 40b, thus to be common to each other. Therefore, the front end of the channel 42 is opened to the outside at the operating portion 8 by the back end 40b. A back end of the channel 42 is communicated with the front end 41a, thus to be common to each other. Further, the back end of the channel 42 is opened to the outside at the operating portion 8. The channel 42 is for suction.

A piping (or tube) from a suction device (not shown) is connected to the back end 41b, and the suction operation is performed by using the suction device. Further, the front end 41a and the back end 40b are closed, thereby sucking the body fluid from the front end 40a through the channels 41, 42, and 40.

A channel 43 is mainly provided in the inserting portion 7. A front end 43a thereof is opened to the outside at the tip portion 17. A back end 43b thereof is opened to the outside at the operating portion 8. The channel 43 is an air/water feed channel which feeds the air and water for cleaning a lens surface of the tip portion 17.

A channel 44 is mainly provided in the connecting cord 9. A front end of the channel 44 is common to the back end 43b, and is opened to the outside near the back end of the operating portion 8. A back end 44b thereof is opened to the outside at the connector portion 10 by the liquid feed cap 24. The back end 43b is closed and the air or water is fed from the back end 44b (liquid feed cap 24), and then the air or water is fed from the front end 43a.

A channel 45 is mainly provided in the inserting portion 7. A front end 45a thereof is opened to the outside at the tip portion 17. A back end 45b thereof is opened to the outside at the operating portion 8.

A channel 46 is mainly provided in the connecting cord 9. A front end 46a thereof is opened at the operating portion 8. A back end 46b thereof is opened to the outside at the connector portion 10 by the injecting cap 26.

The back end 45b and the front end 46a, which are opened to the outside at the operating portion 8, are connected by a connecting tube 47. The connecting tube 47 has a connecting cap which is detachably connected to the back end 45b and the front end 46a.

Referring to FIG. 4A, the channel 45 and the channel 46 form one channel with the back end 45b and the front end 46a connected to each other by the connecting tube 47. The connecting tube 47 may be used as a front water-feeding channel for feeding water to, for example, a subject to be observed. Namely, water is fed from the back end 46b, flows through the channel 46, the connecting tube 47, and the channel 45, and is fed from the front end 45a.

By detaching the connecting tube 47 upon re-processing for enabling reuse after examination, communicating means is formed so that both ends of the channels 45 and 46 are communicated with the outside of the endoscope 2.

That is, according to the conventional art, the channels 46 and 45 form a single elongated channel which is extended to the tip portion 17 of the inserting portion 7 from the connector portion 10. However, according to the first embodiment, the end portions 46a and 45b opened to the outside are formed in the operating portion 8 situated in the neighborhood of substantially the center of the connector portion 10 and the tip portion 17 of the inserting portion 7. When the end portions 46a and 45b are arranged to the operating portion 8, they may be arranged near the center of the entire length of a channel formed by the connector portion 10 and the tip portion 17 of the inserting portion 7.

Upon the endoscope examination, both the ends 46a and 45b are communicated therewith, thereby having a function for feeding the fluid similarly to the conventional art. Further, in re-processing for enabling reuse by cleaning and sterilization, both of the ends 46a and 45b are opened to the outside. Thus, both of the ends 46a and 45b form a channel which is communicated with the outside with the short length of channel, and re-processing ends in a short time.

The route of the channel 46, the connecting tube 47, and the channel 45 varies depending on the type of the endoscope 2 but has a length of 2 to 5 m. The length of the channel should be thin in diameter, such as $\phi 1$ to $\phi 2$ so that the liquid is fed from the front end 45a by using the channel 46, the connecting tube 47, and the channel 45. If not, the large amount of the liquid fed from the back end 46b is necessary or the liquid is not fed from the front end 45a with momentum. A large diameter of the channel is not realized due to other channels and incorporated components (not shown).

The endoscope 2 according to the first embodiment has various channels which are opened at both ends thereof to the outside at the inserting portion 7 or the connector portion 10. In particular, the ends of the thin and elongated channels 45 and 46 are opened adjacently thereto at the operating portion 8, and the channels 45 and 46 are used as one channel by the connection using the connecting tube 47. Further, in re-processing, the cleaning and the sterilization are performed in a short time by detaching the connecting tube 47.

The electric connector portion 11 has an air port 37 which is communicated with the outside of the exterior member of the electric connector portion 11 and an inside space portion thereof. Therefore, in the cleaning operation, the waterproof cap 33 is attached to the electric connector portion 11.

Referring to FIG. 4A, both of the ends 45b and 46a opened at the operating portion 8 are selectively communicated by using the connecting tube 47. In place of it, referring to FIG. 4B, a block-shaped connecting member 39 having a connecting path 38 may connect the ends 45b and 46a which are communicated therewith, or may be disconnected.

The connecting tube 47, particularly, the connecting member 39 has a simple structure containing a non-metallic material such as rubber that is inexpensive. Thus, the connecting tube 47 and the connecting member 39 are not limited to reused members but may be used as a disposable member.

As will be described later (with reference to FIG. 5), upon sterilizing with high-temperature and high-pressure vapor of the endoscope 2, the waterproof cap 33 with the pressure adjusting valve is attached to the electric connector portion 11 according to the first embodiment. In this case, the pressure adjusting valve (not shown) of the waterproof cap 33 is closed, the air port is closed by the waterproof cap 33, and the inside of the endoscope 2 is watertightly closed to the outside.

In the process for the sterilization, the pre-vacuum step and the sterilizing step are executed. By the sterilizing method having the pre-vacuum step, the following processing in the pre-vacuum step is performed.

In the pre-vacuum step, the pressure in the chamber 52 as the sterilizing room reduces, thereby generating the pressure difference that the outside of the endoscope 2 is lower than the inside. Then, the pressure adjusting valve is opened, the inside of the endoscope 2 is communicated with the outside via the air port, and the large pressure-difference is prevented between the inside of the endoscope 2 and the chamber 52. Thus, the pressure difference between the inside and the outside of the endoscope 2 does not damage the endoscope 2.

In the sterilizing step, the chamber 52 is pressurized, causing the pressure difference that the pressure of the outside of the endoscope 2 is higher than that of the inside. Then, the pressure adjusting valve is closed. As a consequence, the waterproof cap 33 prevents the vapor with high temperature and high pressure from actively entering inside of the endoscope 2 via the air port 37.

The exterior member of the endoscope 2 receives the pressure directed to the inside from the outside, which is obtained by adding the pressure reduced in the pre-vacuum step and the pressure increased in the sterilizing step.

The following processing in a pressure reducing step is performed by a method including the pressure reducing step after the sterilizing step.

That is, in the sterilizing step, the pressure of the chamber 52 is reduced, causing the pressure difference that the pressure of the outside of the endoscope 2 is lower than that of the inside. Then the pressure adjusting valve is opened, and the inside of the endoscope 2 is communicated with the outside via the air port 37. This prevents the occurrence of the large pressure difference between the inside of the endoscope 2 and the chamber 52. As a consequence, the endoscope 2 is not damaged due to the pressure difference between the inside and the outside of the endoscope 2.

The pressure reducing step ends, then, the pressure is applied to the chamber 52, and the pressure difference is caused so that the pressure of the outside of the endoscope 2 is higher than that of the inside.

According to the first embodiment, the communicating means is provided to selectively communicate the channels 45 and 46 with the outside of the endoscope 2. As will be described hereinbelow, the communicating means enables the short-time sterilization.

Figure 5:
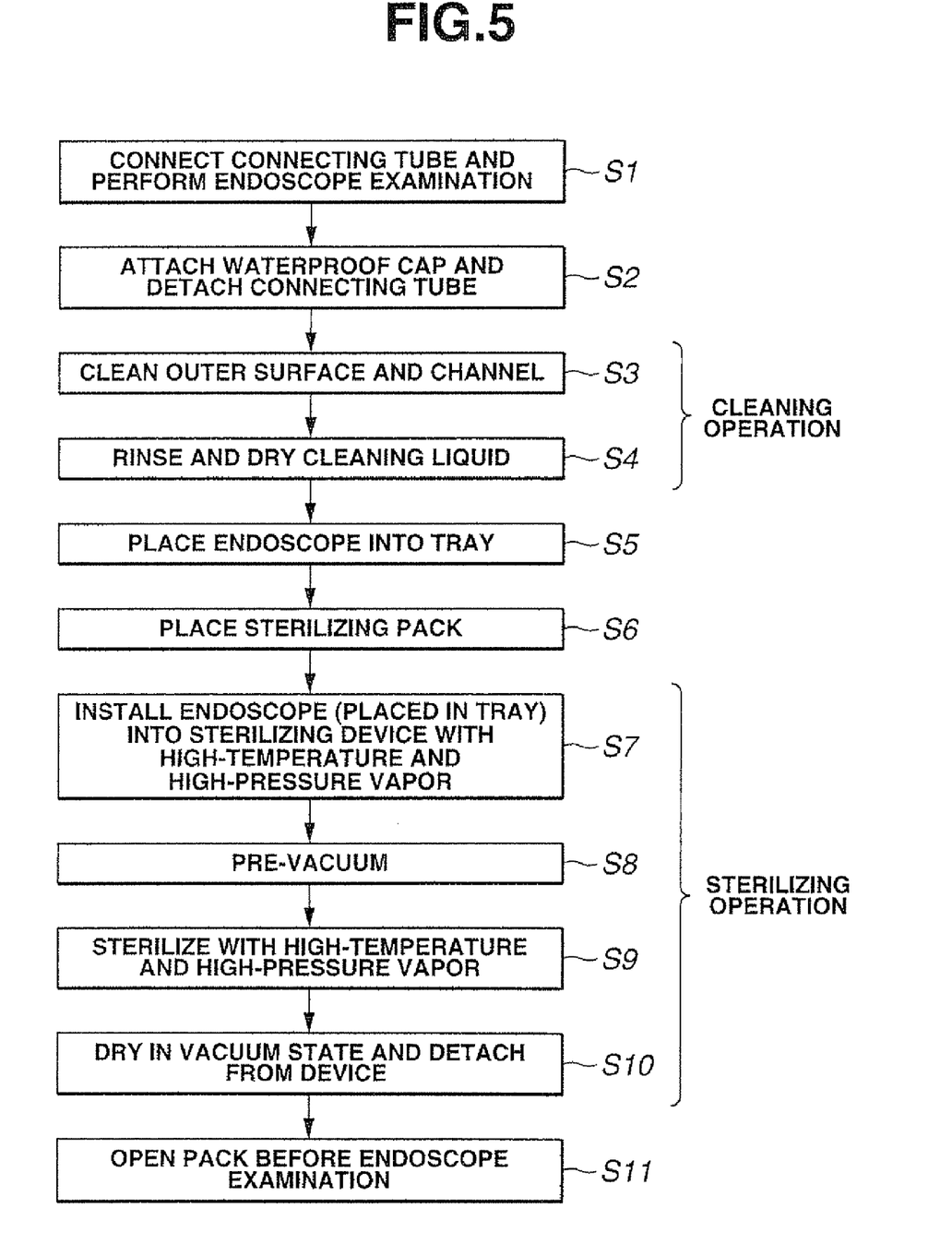
FIG. 5 is a diagram showing in detail the re-processing such as cleaning and sterilization.

Next, a description is given of the operation according to the first embodiment with reference to FIG. 5.

As shown in FIG. 5, upon performing the endoscope examination, the connecting tube 47 (or connecting member 39) is connected, and then the endoscope examination is performed in step S1.

As mentioned above, the connecting tube 47 (or connecting member 39) is connected between the ends 45b and 46a at the operating portion 8 of the endoscope 2, thereby setting the resultant channel as a front water-feeding channel to be available in the endoscope examination.

In the re-processing for enabling reuse after the endoscope examination, the cleaning operation is first performed. In this case, in step S2, the waterproof cap 33 with the pressure adjusting valve is attached to the electric connector portion 11 and the connecting tube 47 (or connecting member 39) is detached.

That is, the waterproof cap 33 is attached to the electric connector portion 11 to watertightly cover the inside of the electric connector portion 11 and the inside of the exterior member of the endoscope 2 is watertight to the outside of the endoscope 2.

In the sterilizing operation after the cleaning operation (which will be described later), the pressure adjusting valve attached to the waterproof cap 33 appropriately functions upon increasing or decreasing the pressure.

By detaching the connecting tube 47 (or connecting member 39), the channels 45 and 46 are cleaned in a short time (in the sterilizing operation, which will be described, the channels 45 and 46 are also easily sterilized in a short time).

Then, in step S3, the outer surface of the endoscope 2 and the channels therein are cleaned.

In step S3, the watertight endoscope 2 is put in a cleaning tank or the like and then the outer surface of the endoscope 2 and the channels therein are cleaned. In the cleaning operation, the channels 45 and 46 form a channel equivalent to that for being communicated with the channels 45 and 46 to the outside with the short length between both ends thereof. In this case, the channel formed by the channels 45 and 46 has low resistant to the cleaning fluid, as compared with the long channel, and is cleaned in a short time.

In step S4, the cleaning fluid is rinsed or dried and then the cleaning operation (cleaning step) ends. In this case, the drying operation similarly ends in a short time.

After ending the cleaning operation, in step S5, the endoscope 2 is placed in the tray 35.

As mentioned above, the endoscope 2 is placed in the tray 35 of the storage case 34, and is closed by the cover member 36. Thereafter, in step S6, the storage case 34 which places therein the endoscope 2 is placed (packed) in a sterilizing pack (peel pack). The storage case 34 is unfailingly packed in the sterilizing pack so as to prevent the entry of bacteria in the air (air and steam pass but the bacteria do not enter).

In steps S7 to S10, sterilization (sterilizing step) is performed. In step S7, the endoscope 2 which is placed in the tray 35 (or the storage case 34) is installed to the sterilizing device 50 with high-temperature and high-pressure vapor shown in FIG. 3.

In the sterilizing operation shown in FIG. 5, the sterilizing device 50 with high-temperature and high-pressure vapor performs the processing in the pre-vacuum step (pressure reducing step) in step S8 before advancing to step S9 as a sterilizing step with high-temperature and high-pressure vapor.

In the sterilizing method having the pre-vacuum step, the pressure in the sterilizing room is reduced and then the pressure difference is caused so that the pressure of the outside of the endoscope 2 is lower than that of the inside. The pressure adjusting valve is opened, and the inside of the endoscope 2 is communicated with the outside via the air port 37, thereby preventing the occurrence of the large pressure difference between the inside of the endoscope 2 and the chamber 52.

In step S9, in the sterilizing step with high-temperature and high-pressure, the pressure of the chamber 52 is increased and then the outside of the endoscope 2 is higher than that of the inside. In this case, the pressure adjusting valve is closed. Thus, the waterproof cap 33 prevents active entry of vapor with high temperature and high pressure inside the endoscope 2 via the air port 37.

The exterior member of the endoscope 2 receives the pressure directed to the inside from the outside, which is obtained by adding the pressure reduced in the pre-vacuum step and the pressure increased in the sterilizing step.

In the sterilizing step with high-temperature and high-pressure vapor, the channels 45 and 46 are formed two short channels which are opened at the operating portion 8. Therefore, the vapor spreads fast throughout the channels 46 and 45. That is, as compared with the conventional art, the channels 46 and 45 are sterilized with high-temperature and high-pressure vapor in a further shorter time.

After the sterilizing step with high-temperature and high-pressure vapor, the pressure reducing step in step S10 is performed (vacuum drying step).

In the pressure reducing step, the pressure of the chamber 52 is reduced and the pressure difference is caused so that the pressure of the outside of the endoscope 2 is lower than that of the inside. Simultaneously, the pressure adjusting valve is opened, and the inside of the endoscope 2 is communicated with the outside via the air port 37, thereby preventing the generation of the large pressure difference between the inside and the outside of the endoscope 2. Thus, the endoscope 2 is not damaged due to the pressure difference between the inside and the outside thereof. The endoscope dries in the pressure reducing step.

After the endoscope is dried in the pressure reducing step, the pressure in the chamber 52 is increased and returned to a normal pressure. In this case, the pressure difference is caused so that the pressure of the outside of the endoscope 2 is higher than that of the inside, and the pressure adjusting valve is closed.

After that, the endoscope 2 covered with the sterilizing pack is taken out from the sterilizing device 50 with high-temperature and high-pressure vapor.

In step S11, the sterilizing pack is opened before the endoscope examination, and the endoscope 2 sterilized and placed in the storage case 34 is taken out. Then, as shown in step S1, the connecting tube 47 is connected, thus to reuse the endoscope 2 for endoscope examination.

According to the first embodiment, the connecting tube 47 (or connecting member 39) is detached in the re-processing, thereby dividing a channel having the long length between both ends thereof into two short channels. Consequently, the cleaning operation and the vapor sterilization of the channels may be completed in a short time.

A complementary description is given of the case of the vapor sterilization as follows.

That is, in the sterilizing step with high-temperature and high-pressure vapor, the endoscope 2 is placed in the chamber 52 in the sterilizing device 50 with high-temperature and high-pressure vapor shown in FIG. 3, and is sterilized by vapor with high temperature and high pressure fed into the chamber 52.

In this case, the vapor needs to sufficiently be spread in the channels as shown in FIG. 4A.

In order to sufficiently spread the vapor in the channels, a channel with the large diameter and the short length enables the fast and efficient sterilization. However, the channels shown in FIG. 4A, particularly, the channels including the channel 46, the connecting tube 47, and the channel 45 form a long and small diameter channel. Therefore, it is difficult to enable the vapor to sufficiently be spread in the entire channels and thus to sterilize the channel in a short time.

However, with the structure, the connecting tube 47 is detached in the sterilizing step, and the channels are opened. Thus, the channels 46 and 45 of the endoscope 2 become short channels and are communicated with the outside. The vapor is fed to the channels 46 and 45 in a short time and the sterilization may end in a shorter time, as compared with the conventional art, in which the single channel is communicated with the outside.

In this case, by arranging the connecting members, e.g., the connecting tube 47 or the connecting member 39 (connecting path 38) to the operating portion 8, the connecting tube 47 or the connecting member 39 (connecting path 38) may be set so as to locate in the neighborhood of substantially the center of the channel 45 and the channel 46. As compared with the case in which the connecting tube 47 or the connecting member 39 (connecting path 38) is arranged at the position except for that near the center, the channels 45 and 46 are subjected to efficient vapor sterilization.

When the operator uses the endoscope 2 for endoscope examination, the connecting tube 47 or the connecting member 39 is connected to the endoscope 2 and endoscope 2 is used. Thus, the channels 46 and 45 become one channel and liquid can be fed from the front end 45a with the necessary momentum by feeding the liquid from the back end 46b.

By using the connecting tube 47 or the connecting member 39 as an inexpensive disposal member, cleaning, disinfection, and sterilization of the connecting tube 47 or the connecting member 39 can be omitted, and simple cleaning, disinfecting, and sterilizing means is provided.

According to the first embodiment, advantageously, the channels included in the endoscope 2 can be sterilized more quickly.

Second Embodiment

Figure 6:
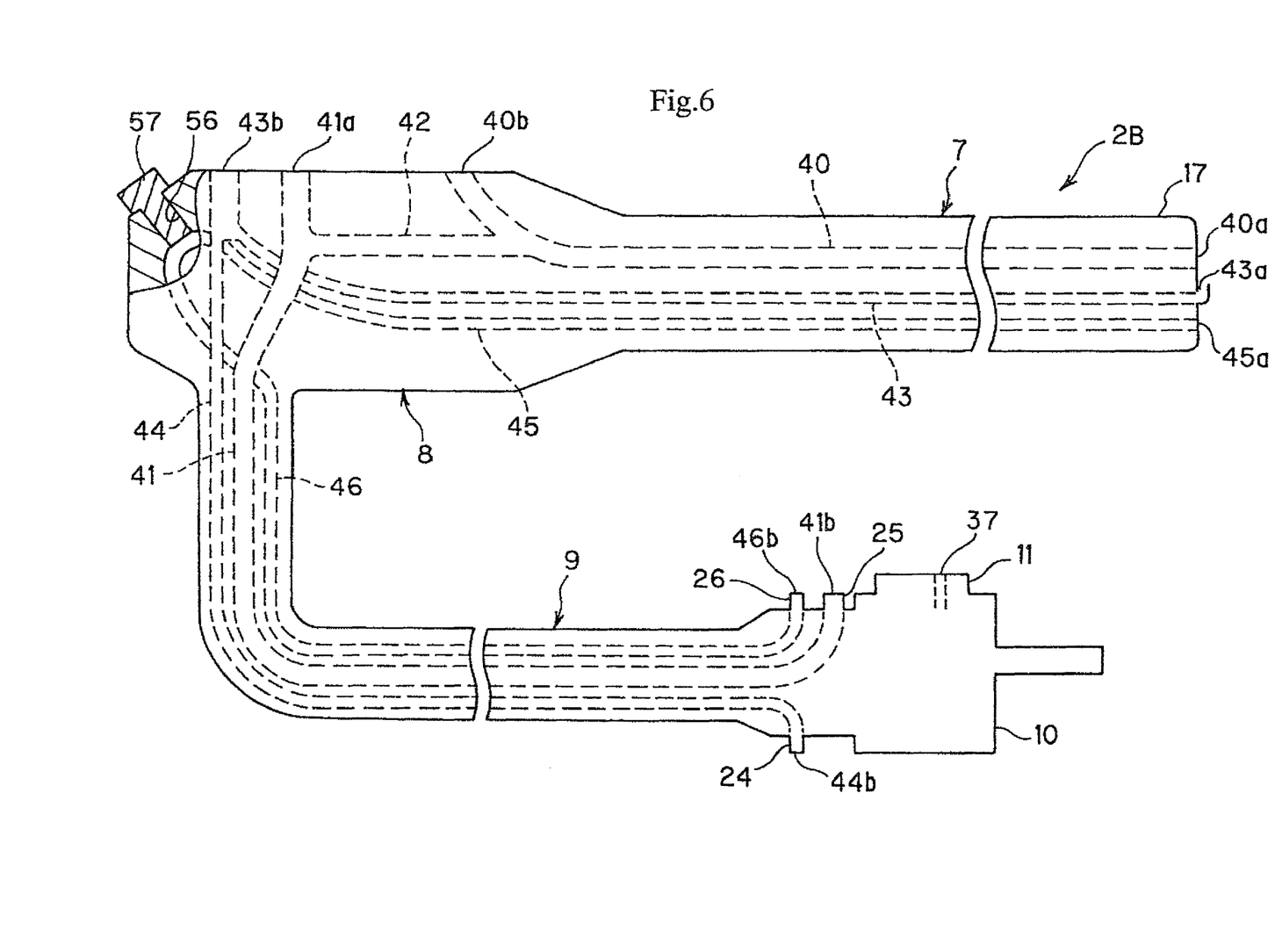
FIG. 6 is a diagram schematically showing a channel system of an endoscope according to a second embodiment.

Next, a description is given of the second embodiment of the present invention with reference to FIG. 6. FIG. 6 schematically shows a channel system in an endoscope 2B according to the second embodiment. According to the second embodiment, the back end 45a of the channel 45 and the front end 46b of the channel 46 in the first embodiment are communicated therewith so that they form a single channel inside of the operating portion 8. Further, a communicating path 56 is formed so that the channel which is disposed inside of the operating portion 8 is communicated with the outside of the operating portion 8.

Specifically, referring to FIG. 6, the channel 45 is mainly provided in the inserting portion 7. The front end 45a is opened to the outside at the tip portion 17. The back end side is connected to the communicating path 56.

The channel 46 is mainly provided in the connecting cord 9. The front end is connected to the communicating path 56 common with the channel 45. The back end 46b is opened to the outside at the connector portion 10 by using the injecting cap 26.

The communicating path 56 is normally closed by a stop valve 57 (except for the cleaning step or sterilizing step). By closing the communicating path 56, a route of the channel 48 and the channel 44 is used as a channel for feeding water which feeds liquid to the observing target from the front end 44a by feeding the liquid from the back end 44b. Other structures are the same as those according to the first embodiment.

Next, the operation according to the second embodiment will be described.

In the sterilizing step with high-temperature and high-pressure vapor, when the endoscope 2B is sterilized with high-temperature and high-pressure vapor fed into the chamber 52 of the sterilizing device 50 with high-temperature and high-pressure vapor shown in FIG. 3, the vapor needs to be spread in the channels shown in FIG. 6.

With the structure, the stop valve 57 is detached and the communicating path 56 is opened in the sterilization. Thus, the vapor is sufficiently spread to the channels 46 and 45 quickly.

Upon using the endoscope 2B, the operator closes the communicating path 56 by the stop valve 57 and uses the endoscope 2B. Consequently, the channels 46 and 45 form one channel and, by feeding the liquid from the back end 46b, the liquid spouts out from the front end 45a with the necessary momentum.

The stop valve 57 for closing the communicating path 56 may be provided so as to close the entire communicating path 56. Thus, an uneven portion made at the connecting portion between the channels 46 and 45 is suppressed. Upon feeding the liquid from the back end 46b, the liquid passes through the channel 46 to the channel 45 with minimum amount of resistant change in the channel at the connecting portion. The loss in the speed of flow can be reduced when the liquid passes through the connecting portion of the channels, and the liquid spouts out from the front end 45a with the sufficient momentum.

By arranging the communicating path 56 to the operating portion 8, the communicating path 56 is arranged near the center of a channel formed by the channels 45 and 46. Thus, the vapor can be efficiently spread throughout the channels 45 and 46 in the sterilizing step with high-temperature and high-pressure vapor.

Further, by arranging the communicating path 56 in the operating portion 8, the projecting shape of the stop valve 57 extended from the operating portion 8 is small and the preferable operability is obtained upon gripping and operating the operating portion 8 for examination by the operator.

According to the second embodiment, advantageously, the sterilization of the channels included in the endoscope 2B can be performed quickly.

Third Embodiment

Next, the third embodiment of the present invention will be described with reference to FIGS. 7A and 7B.

Figure 7A:
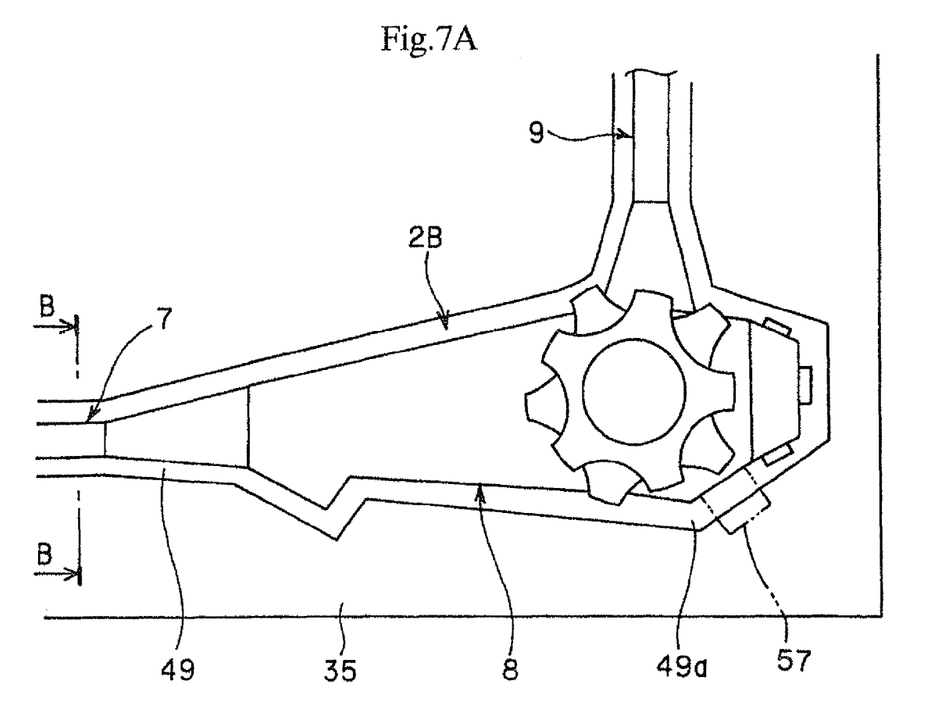
FIG. 7A is a diagram showing a portion near an operating portion when the endoscope is placed in a regulating portion in a tray.
Figure 7B:
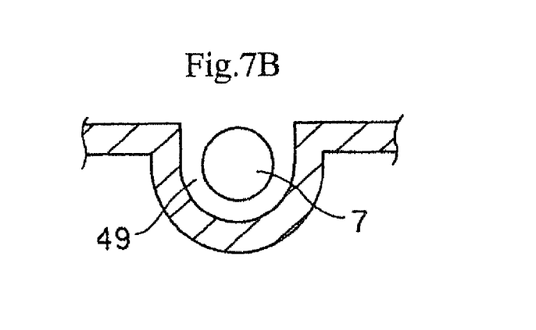
FIG. 7B is a cross-sectional view showing a B-B cross section shown in FIG. 7A.

FIG. 7A shows a portion near the operating portion 8 when the endoscope 2B is placed in the regulating portion 49 of the tray 35.

After ending the endoscope examination, the endoscope 2B is cleaned. Then, the endoscope 2B is placed in the tray 35 as shown FIG. 2 with a predetermined shape so as to perform the sterilizing step with high-temperature and high-pressure vapor after the cleaning.

In this case, the regulating portion 49a near the operating portion 8 has a concaved portion along the shape of the operating portion 8 as shown in FIG. 7A. On the contrary, if the stop valve 57 attached to the operating portion 8 is not completely detached from the operating portion 8, the stop valve 57 is projected and the operating portion 8 is not placed in the tray 35.

According to the third embodiment, when the sterilizing device 50 with high-temperature and high-pressure vapor shown in FIG. 3 places therein the storage case 34 of the tray 35 which places therein the endoscope 2B and the sterilization is executed, the chamber 52 just places therein only one storage case 34 which places therein the endoscope 2B.

Other structures are the same as those according to the second embodiment.

Next, a description is given of the operation according to third embodiment.

When the endoscope 2B is placed in the tray 35 while the stop valve 57 is attached to the operating portion 8, a projected portion of the operating portion 8 interferes to the regulating portion 49a and therefore the endoscope 2B is not completely placed in the tray 35. Since the endoscope 2B is completely placed in the tray 35 when the stop valve 57 is detached from the operating portion 8, the omission of detachment of the stop valve 57 is prevented. That is, the regulating portion 49a constitutes means for confirming the omission of detachment of the stop valve 57 or means for notifying the omission of detachment of the stop valve 57 to the user.

Even when the endoscope 2B is not completely placed in the tray 35 and the user installs the tray 35 into the sterilizing device 50 with the high-temperature and high-pressure vapor, the tray 35 is not completely installed into the chamber 52. This constitutes confirming means which confirms whether or not the user ensures the state in which the channels 46 and 45 are communicated with the outside at the operating portion 8.

Thus, in addition to the advantages according to the second embodiment, the sterilization is certainly performed in the proper state.

The third embodiment uses the endoscope 2B shown in FIG. 6. However, the third embodiment can be applied to the endoscope 2 according to the first embodiment.

It should be understood that the present invention is not limited to those embodiments and various changes and modifications thereof could be made without departing from the spirit of scope of the invention as defined in the appended claims.

What is claimed is:

1. An endoscope comprising:
an operating portion;
an inserting portion defining a first channel, the first channel having a first channel front-end which is open to the outside at a distal end of the inserting portion and a first channel back-end which is open on an outer surface at the operating portion;
a connecting cord defining a second channel, the second channel having a second channel front-end which is open on the outer surface at the operating portion and a second channel back-end which is open to the outside at a connector portion of the connecting cord; and
a channel-connecting member comprising a tubular portion projecting from the outer surface of the operating portion, the tubular portion defining a connecting channel, the channel-connecting member being adapted to detachably connect the first channel back-end and the second channel front-end to place the first channel and the second channel in communication via the connecting channel.

2. The endoscope according to claim 1, wherein the channel-connecting member is one connecting tube in which is formed a connecting path having one end opening to be connected to the first channel back-end and another end opening to be connected to the second channel front-end.

3. The endoscope according to claim 2, wherein the one end opening and the another end opening are each provided with a connecting cap to allow detachable connection of the connecting tube.

4. The endoscope according to claim 2, wherein the channel-connecting member is formed such that only a portion for forming the connecting path and a gripping portion necessary for attaching/detaching operations of the channel-connecting member are projected and exposed on the outer surface of the operating portion.

5. The endoscope according to claim 1, wherein the channel-connecting member has one end opening to be connected to the first channel back-end and another end opening to be connected to the second channel front-end, the channel-connecting member further having a connecting path formed therein over the one end, opening and the another end opening to connect between the first channel back-end and the second channel front-end.

6. The endoscope according to claim 1, wherein the channel is for spouting out cleaning fluid and air from a spouting opening formed at a distal end of an inserting portion of the endoscope, or for sucking fluid in the body cavity from a suction opening formed to the inserting portion.

7. The endoscope according to claim 1, further comprising a notification means for notifying omission of detachment of the channel-connecting member in placing the endoscope in a sterilization storage case, the notification being performed in that, if the channel-connecting member is attached to the operating portion when placing the endoscope in the sterilization storage case to sterilize endoscope with the vapor, the channel-connecting member projecting from an outer surface of the operating portion interferes with the notification means when placing the endoscope in the sterilization storage case, and thus prevents the endoscope from being completely placed in the case.

8. The endoscope according to claim 1, wherein the first channel back-end and the second channel front-end are placed adjacent to each other on the outer surface of the operating portion.

9. A method for sterilizing an endoscope with high-temperature and high-pressure vapor the endoscope comprising:
   an operating portion;
   an inserting portion defining a first channel, the first channel having a first channel front-end which is open to the outside at a distal end of the inserting portion and a first channel back-end which is open on an outer surface at the operating portion;
   a connecting cord defining a second channel, the second channel having a second channel front-end which is open on the outer surface at the operating portion and a second channel back-end which is open to the outside at a connector portion of the connecting cord; and
   a channel-connecting member comprising a tubular portion projecting from the outer surface of the operating portion, the tubular portion defining a connecting channel, the channel-connecting member being adapted to detachably connect the first channel back-end and the second channel front-end to place the first channel and the second channel in communication via the connecting channel the method comprising:
a detaching step of detaching the channel-connecting member from the operating portion so that the operating portion is unattached with the channel-connecting member, to open the first channel back-end and the second channel front-end; and
a sterilization step for vapor sterilization by introducing the vapor into the channel from the first channel back-end and the second channel front-end exposed by the detaching step.

* * * * *